(12) United States Patent (10) Patent No.: US 9,320,562 B2
Kienzle et al. (45) Date of Patent: Apr. 26, 2016

(54) SURGICAL INSTRUMENT

(75) Inventors: Karl-Ernst Kienzle, Tuttlingen (DE);
Dieter Weisshaupt, Immendingen (DE)

(73) Assignee: Aesculap AG, Tuttlingen (DE)

( * ) Notice: Subject to any disclaimer, the term of this patent is extended or adjusted under 35 U.S.C. 154(b) by 741 days.

(21) Appl. No.: 13/135,727

(22) Filed: Jul. 12, 2011

(65) Prior Publication Data

US 2012/0004685 A1 Jan. 5, 2012

Related U.S. Application Data

(63) Continuation of application No. PCT/EP2009/064505, filed on Nov. 3, 2009.

(30) Foreign Application Priority Data

Feb. 3, 2009 (DE) .......................... 10 2009 007 205

(51) Int. Cl.
*A61B 18/14* (2006.01)
*A61B 17/30* (2006.01)
*A61B 17/00* (2006.01)
*A61B 17/28* (2006.01)

(52) U.S. Cl.
CPC ............ *A61B 18/1442* (2013.01); *A61B 17/30* (2013.01); *A61B 2017/0046* (2013.01); *A61B 2017/2825* (2013.01); *A61B 2018/1462* (2013.01)

(58) Field of Classification Search
CPC ............ A61B 17/30; A61B 2017/305; A61B 2017/0046; A61B 2017/00473; A61B 2017/2825; A61B 2018/1462; A61B 2018/1442
USPC ................................. 606/205–211
See application file for complete search history.

(56) References Cited

U.S. PATENT DOCUMENTS

| | | | |
|---|---|---|---|
| 3,322,124 A * | 5/1967 | Ireland ......................... 433/141 |
| 4,452,106 A | 6/1984 | Tartaglia |
| 4,592,347 A * | 6/1986 | Mahruki ....................... 606/206 |
| 5,152,778 A * | 10/1992 | Bales et al. ................... 606/205 |
| 5,275,322 A * | 1/1994 | Brinkerhoff et al. ...... 227/175.1 |
| 5,334,215 A | 8/1994 | Chen |
| 5,653,713 A * | 8/1997 | Michelson ...................... 606/83 |
| 5,893,875 A * | 4/1999 | O'Connor et al. ............ 606/205 |
| 5,947,996 A * | 9/1999 | Logeman ..................... 606/205 |

(Continued)

FOREIGN PATENT DOCUMENTS

| | | |
|---|---|---|
| DE | 32 45 570 | 6/1984 |
| DE | 20 2007 016 233 | 3/2008 |

(Continued)

*Primary Examiner* — Alexander Orkin
(74) *Attorney, Agent, or Firm* — Lipsitz & McAllister, LLC

(57) ABSTRACT

A surgical instrument with two legs movable relative to each other is provided. A tip inserted in a receiving space at the distal end of each leg is exchangeably held at the free end of the leg. A two part fixing device is provided for releasable fixation of the tip to the leg, the fixing device having on one of the parts two locking arms which are arranged next to each other and are elastically bendable apart, and on the other of the parts a locking projection extending into the leg transversely to the direction of insertion. The locking projection, when inserting the tip into the receiving space, engages between the locking arms, bending them apart, and at the end of the inserting movement, enters a recess on the inner side of the locking arms. The receiving space widens in the proximal direction from its insertion end.

15 Claims, 6 Drawing Sheets

(56) References Cited

U.S. PATENT DOCUMENTS

| | | | |
|---|---|---|---|
| 6,077,290 A * | 6/2000 | Marini | 606/205 |
| 6,258,107 B1 * | 7/2001 | Balazs et al. | 606/153 |
| 6,860,882 B2 | 3/2005 | Battles et al. | |
| 9,017,369 B2 * | 4/2015 | Renger et al. | 606/205 |
| 2007/0167939 A1 * | 7/2007 | Duong et al. | 606/23 |
| 2009/0043316 A1 * | 2/2009 | Durgin et al. | 606/142 |

FOREIGN PATENT DOCUMENTS

| | | |
|---|---|---|
| EP | 2 011 447 | 1/2009 |
| WO | 97/47249 | 12/1997 |
| WO | 2008/071750 | 6/2008 |

* cited by examiner

SURGICAL INSTRUMENT

This application is a continuation of international application number PCT/EP2009/064505 filed on Nov. 3, 2009 and claims the benefit of German application number 10 2009 007 205.5 filed on Feb. 3, 2009.

The present disclosure relates to the subject matter disclosed in international application number PCT/EP2009/064505 of Nov. 3, 2009 and German application number 10 2009 007 205.5 of Feb. 3, 2009, which are incorporated herein by reference in their entirety and for all purposes.

BACKGROUND OF THE INVENTION

The invention relates to a surgical instrument with two legs movable relative to each other, a tip inserted in a receiving space at the distal end of the leg being exchangeably held at the free end of the legs, with a fixing device for releasable fixation to the leg, the fixing device comprising on one of the two parts two locking arms which are arranged next to each other and are elastically bendable apart, and comprising on the other one of the two parts a locking projection extending into the leg transversely to the direction of insertion of the tip, the locking projection, when inserting the tip into the receiving space of the leg, engaging between the two locking arms, bending these elastically apart, and at the end of the inserting movement, entering a recess on the inner side of the locking arms, so that the locking arms approach each other again after they have been elastically bent apart.

Surgical instruments of this kind are known. These are used as forceps or as clamping instrument, for example, and the tips therein are exchangeable. For example, surgical forceps are described in DE 20 2007 016 233 U1, in which the tip inserted in the receiving space of the leg is, on the one hand, rotated into the correct angular position in relation to the leg by means of special bearing surfaces, and, on the other hand, is fixed in the axial direction by a separate locking device. However, the structure is relatively complicated as separate means are required, on the one hand, for aligning the tip about the longitudinal axis of the leg and, on the other hand, for securing the tip against displacement in the longitudinal direction of the leg.

Forceps are described in U.S. Pat. No. 6,860,882 B2, in which a tip is held exchangeably on a forceps body. To enable the locking arms of the forceps tip to spring out, the receiving space of the forceps body must be broken open at the sides. This results in a reduction in stability, and, in addition, there is a risk of soiling and injury occurring in this region of the openings.

The object of the invention is to simplify a generic surgical instrument in its structure and, in particular, to reduce soiling and risk of injury.

SUMMARY OF THE INVENTION

This object is accomplished, in accordance with the invention, in a surgical instrument of the kind described at the outset, in that the receiving space widens in the proximal direction from its insertion end.

Herein the locking arms, which receive the locking projection between them, assume a double function. When the locking projection enters between the locking arms, these are bent open elastically, and the two locking arms are thereby aligned relative to the locking projection, i.e., the angular position of the tip is thereby fixed in relation to the leg. Once the locking projection engages in the recess, the tip is thereby additionally fixed in the axial direction, i.e., in the direction of insertion. The described configuration has the advantage that the user can insert the tip into the receiving space, during the insertion the tip is aligned relative to the locking projection by rotation about the longitudinal axis of the leg, and once the locking projection snaps into the recess, the user thereby receives feedback, for he feels the snapping of the locking projection into the recess and the thus possible return movement of the elastically bent open locking arms into the initial position.

Owing to the widening of the receiving space in the proximal direction, the receiving space can be closed at the sides, but nevertheless the locking arms of the one part can spring out when the two parts are pushed together. The closed receiving space ensures that no injury or soiling can occur owing to wall openings in the region of the receiving space.

In particular, the inner wall of the receiving space may widen conically from the insertion end in the proximal direction.

It is advantageous for the locking arms to have on their inner side between their free end and the recess a slide surface extending obliquely in relation to the direction of insertion, so that the mutual spacing between the two slide surfaces facing each other increases in the direction towards the free end of the locking arms. Owing to these slide surfaces, the introduction of the locking projection into the space between the two locking arms is facilitated, on the one hand, and, on the other hand, these slide surfaces serve as orientation for the locking arms and therefore for the tip relative to the leg, as the locking projection comes to bear against the slide surfaces and thereby rotates these about the longitudinal axis of the tip relative to the leg in such a way that the desired orientation of the tip relative to the leg occurs.

In accordance with a particularly preferred embodiment of the invention, it is provided that the spacing between the continuations of the recess that are closer to the free end of the locking arms into the inner side of the locking arm is greater than the spacing between the continuations of the recess that are remote from the free end into the inner side of the locking arm. In other words, the step between the recess and the slide surface is lower for the locking projection on the side of the recess facing the free end than on the side of the recess facing away from the free end. The locking projection is thereby blocked against being pushed further forward when it snaps into the recess, i.e., the locking projection acts as end stop for insertion of the tip into the receiving space, but in the reverse direction the locking projection can slide along this step facing the free end, so that when the tip is pushed in, the locking projection can snap into the recess and, conversely, when the tip is pulled out of the receiving space with force, the reverse procedure occurs.

In particular, the locking projection may be a pin extending transversely to the direction of insertion.

It is expedient for the locking projection to have a circular cross section. The recess may, in particular, have the cross section of a segment of a circle.

In these cases, it is advantageous for the radius of the circular projection and of the segment of a circle of the recesses to be substantially identical, so that when it enters the recesses, the locking projection bears with surface-to-surface contact on these.

While it is, in principle, possible to provide the locking projection on the tip and the locking arms with the recesses on the leg, an embodiment is preferred, in which the locking arms are firmly connected to the tip and the locking projection is firmly connected to the leg.

In particular, the locking arms may be formed integrally with the tip or with a holder of the tip and may be separated from each other by a slot extending from the free end of the locking arms beyond the recesses. The manufacture is thereby facilitated. It is sufficient to separate the two locking arms from each other by formation of the slot.

The locking projection may, in particular, extend transversely through the receiving space. Thus, it may, for example, be a pin which is mounted in corresponding receiving openings in the wall of the receiving space.

It is advantageous for the receiving space, at its insertion end at the distal end of the leg, to bear tightly against the outside of the tip inserted in the receiving space. This provides lateral guidance for the tip in the receiving space in this region.

Provision is made in a preferred embodiment for the gap between the tip inserted in the receiving space and the distal end of the leg to be covered by a sealing collar.

It is expedient for the sealing collar to be secured in the direction of insertion of the tip by a locking connection comprising a fixing recess and a fixing projection engaging in the fixing recess. For example, the fixing recess may be a circumferential groove, and the fixing projection a circumferential ring shoulder, and the fixing recess may be located in both the leg and the tip. If the fixing recess is located in the tip, it is expedient, when exchanging the tip, for the sealing collar to be removed with the tip from the leg and thus also exchanged.

The following description of preferred embodiments of the invention serves in conjunction with the drawings for further explanation.

DETAILED DESCRIPTION OF THE INVENTION

Figure 1:
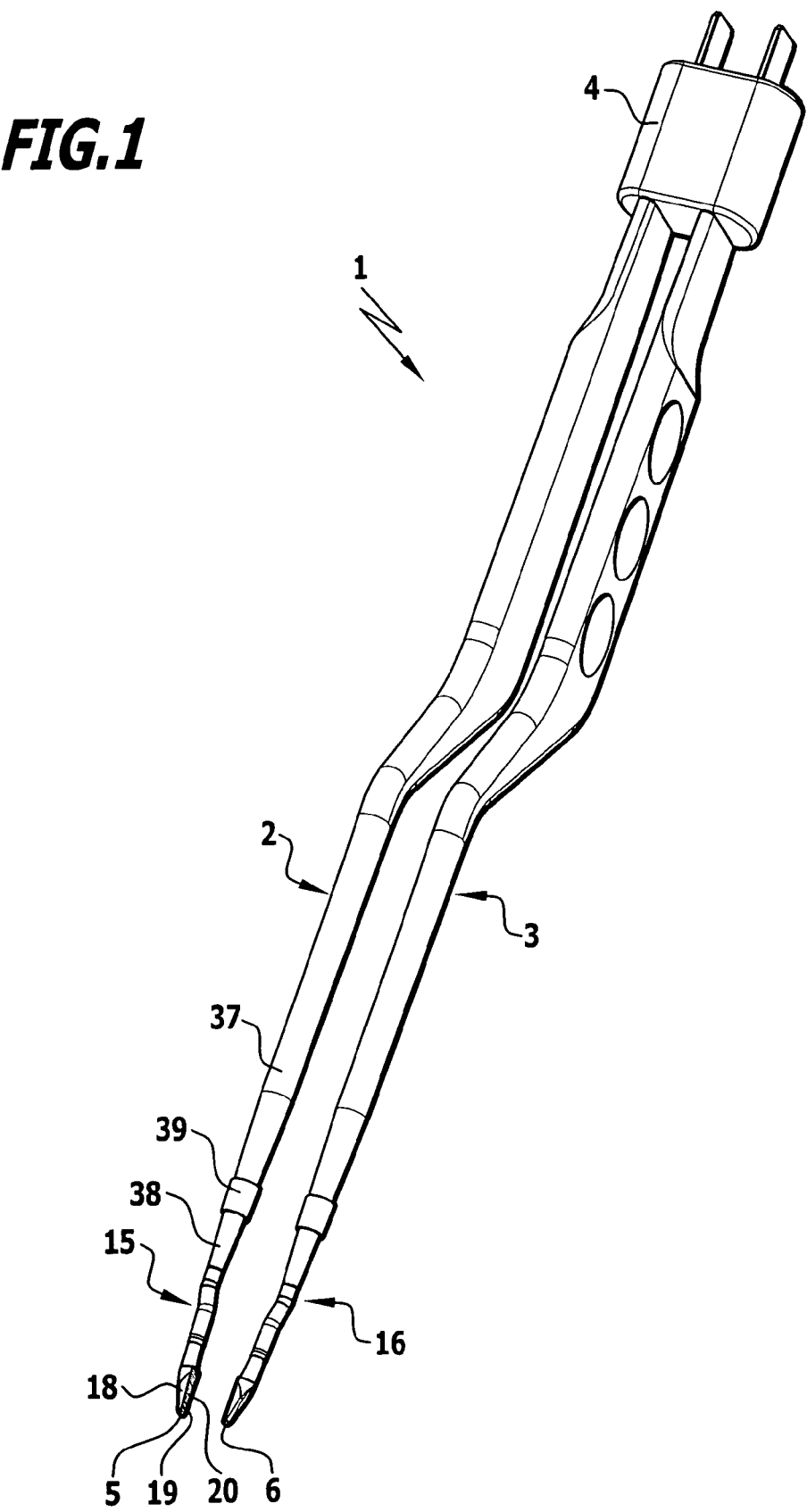
FIG. 1 shows a perspective view of forceps with two legs and tips held exchangeably thereon.
Figure 2:
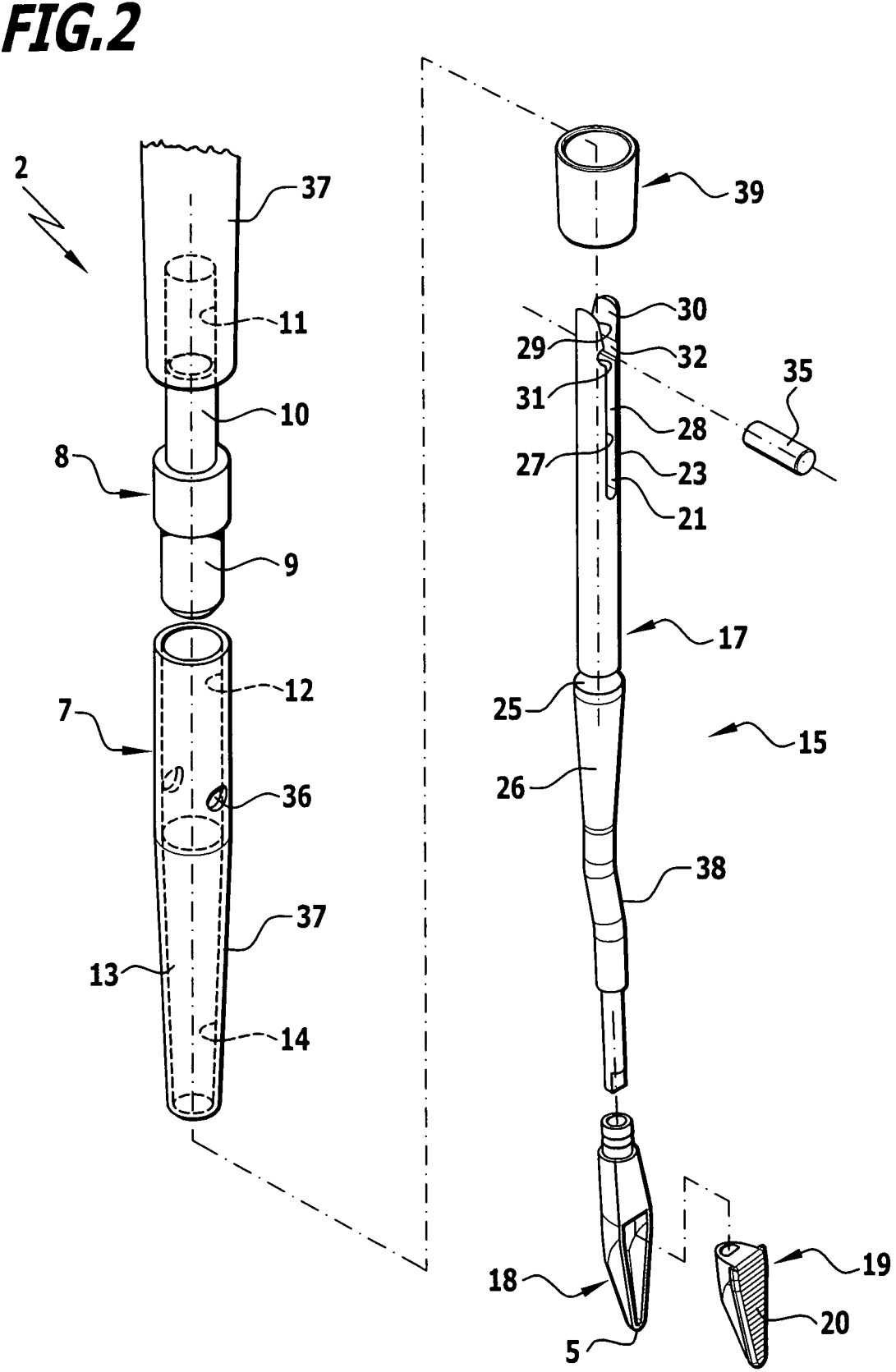
FIG. 2 shows an enlarged detailed view of the distal end of a leg with a receiving space and with the parts of the tip that are insertable into the receiving space.
Figure 3:
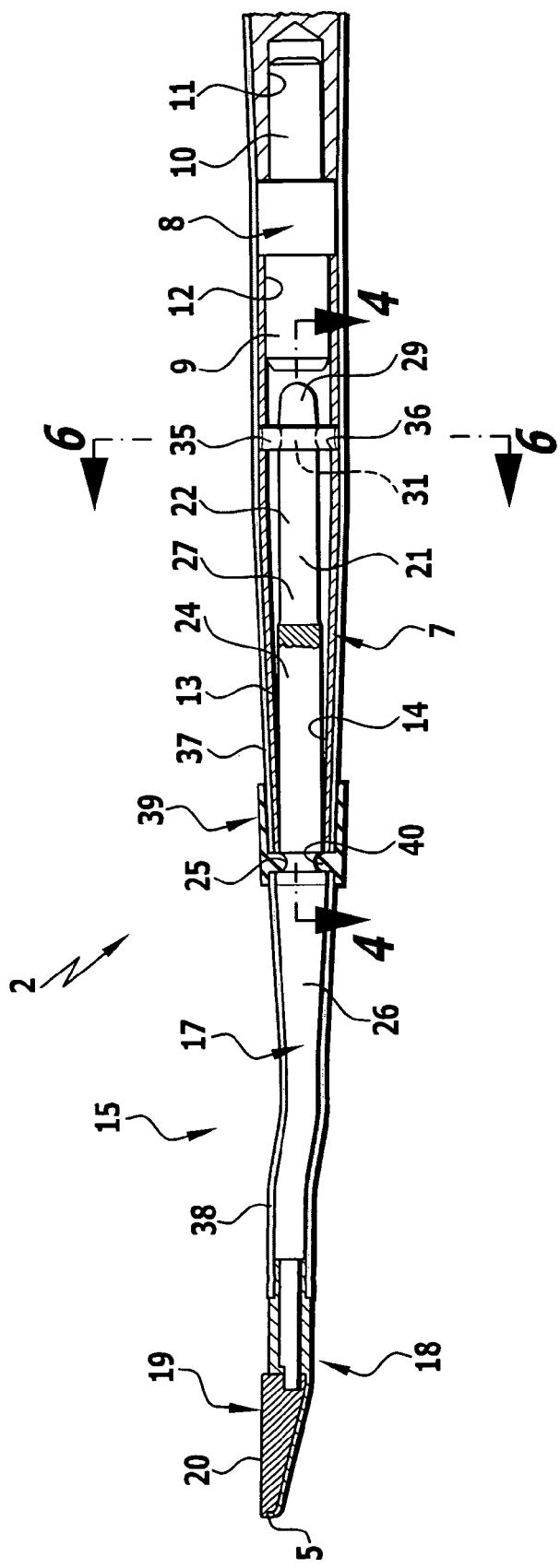
FIG. 3 shows a longitudinal sectional view of the distal end region of a leg with inserted tip.
Figure 4:
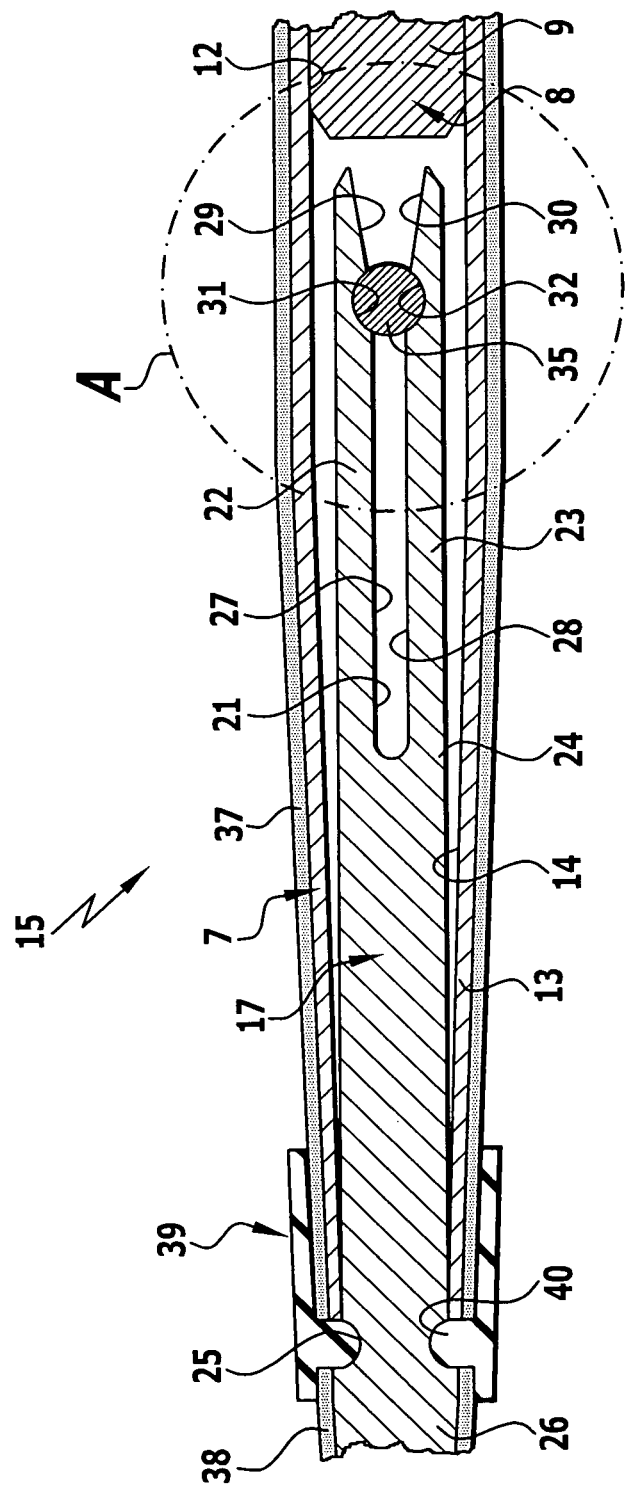
FIG. 4 shows a sectional view taken along line 4-4 in FIG. 3.

The invention is discussed below with reference to forceps 1 as an example. In principle, the invention may, however, be applied to other surgical instruments in which there is held on a leg an exchangeable tip which can be connected to the leg by insertion into a receiving space of the leg, for example, in a clamping tool or in a tong-like instrument.

The forceps 1 comprise two elongate legs 2, 3 arranged next to each other, which are fixed in spaced relation to each other by a connector element 4 at their proximal end and each carry a working element 5, 6 at their distal end.

The legs 2, 3 are elastically resiliently pressable against each other and can also be elastically resiliently pressed apart, so that the two working elements 5, 6 can also be correspondingly moved towards each other or apart.

The two legs 2, 3 are of substantially identical construction in their distal region. Therefore, only one of the two legs will be described in detail below. The leg 2 has at its distal end a sleeve-shaped extension 7, which is connected by an intermediate piece 8 to the respective leg 2. With peg-shaped sections 9, 10 on opposite sides, the intermediate piece 8 engages in corresponding cylindrical regions 11 and 12, respectively, of the leg 2 and the extension 7, respectively. The peg-shaped sections 9, 10 may be screwed into the cylindrical regions 11, 12 or firmly connected to these in some other way, for example, by adhesive bonding.

The sleeve-shaped extension 7 is of cylindrical configuration in a proximal region adjoining the intermediate piece 8. Adjoining this cylindrical region is a conical region 13 whose cross section decreases in the distal direction. The extension 7 thus encloses a receiving space 14, which first widens conically from the distal end of the extension 7 and then continues cylindrically.

Inserted in this receiving space 14 is a tip 15 or 16, which is exchangeably fixed therein.

The tip 15 and, in the same way, the tip 16 are comprised of various parts, i.e., first a holder 17 in the form of an elongate rod and a jaw part 18, which is fitted to the distal end of the holder 17 and is firmly connected to it there. In the illustrated embodiment, there is inserted in the jaw part 18 a clamping insert 19, which has a clamping surface 20. The clamping surfaces 20 of the jaw parts 18, arranged next to each other, of the two legs 2, 3 face each other.

At its proximal end, there is machined in the holder 17 of circular-cylindrical cross section a diametrical, continuous slot 21, which extends parallel to the longitudinal axis of the holder 17 and divides the holder 17 into two arms 22, 23 lying next to each other. In the embodiment shown, the length of the thus produced arms 22, 23 is approximately half as large as the length of a cylindrical, proximal section 24 of the holder 17. Adjoining the distal end of this cylindrical section 24 and extending around it is a circumferential groove 25. Distally, this circumferential groove 25 is followed by a section 26 which tapers conically towards the distal end, with its conicity preferably corresponding to the conicity of the conical region 13 of the extension 7.

Starting from the distal end of the slot 21, the inner sides 27, 28 of the two arms 22, 23 first extend parallel to each other and then continue in the region of the proximal end of the arms 22, 23 into oblique slide surfaces 29, 30, so that the width of the slot 21 widens towards the proximal end of the arms 22, 23.

Figure 5:
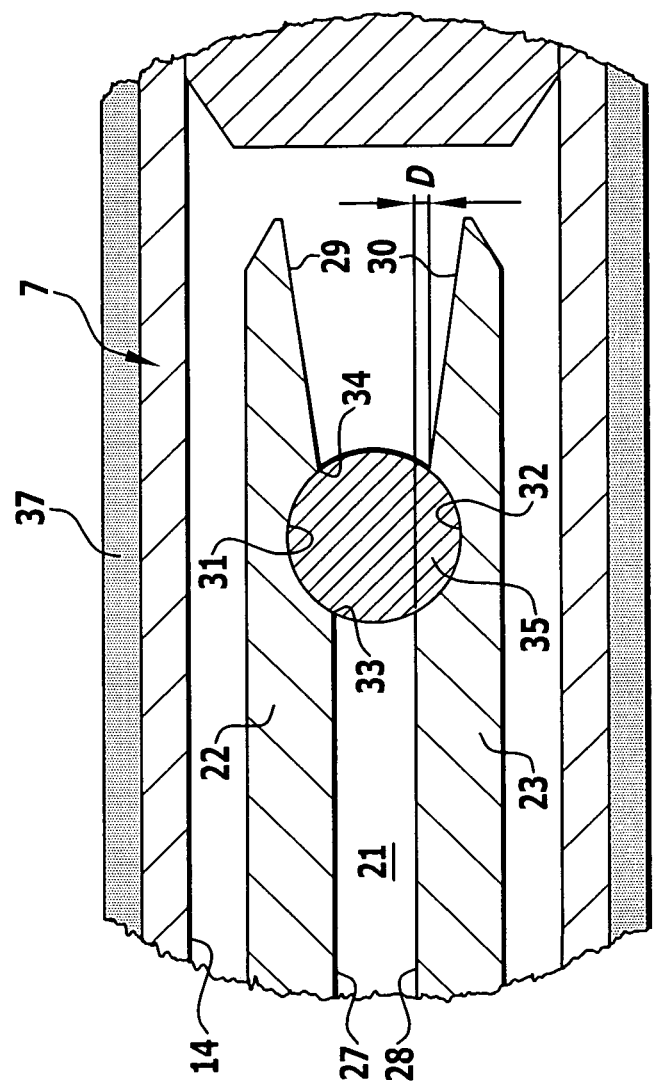
FIG. 5 shows an enlarged detailed view of area A in FIG. 4.
Figure 6:
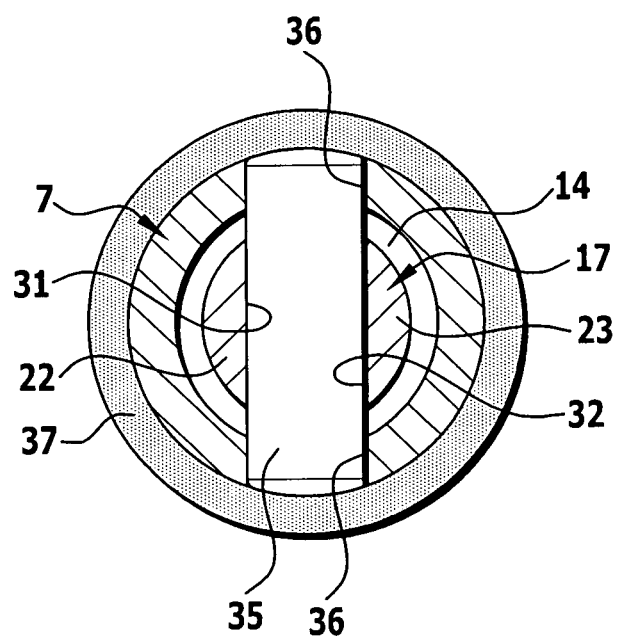
FIG. 6 shows a sectional view taken along line 6-6 in FIG. 3.

In the area of transition between the regions of the inner sides 27 and 28 that extend parallel to each other and the adjoining slide surfaces 29, 30 there is provided in each of the two arms on their inner side a recess 31, 32 extending transversely to the longitudinal direction of the arms 22, 23. The cross section of these recesses 31, 32 has the shape of a segment of a circle, i.e., the bottom of the recesses 31, 32 follows a cross section in the shape of a circular arc, which at the distal end of the recess 31, 32 continues via an edge 33 into the inner side 27 of the arm 22, but at the proximal end of the recess 31 via an edge 34 into the corresponding adjoining slide surface 29. As a result, the edges 33 of the two legs 2, 3 lie closer together than the proximal edges 34 when the arms 22, 23 are undeformed. In FIG. 5, the different height of the edges 33 and 34 is indicated by the difference D.

In the cylindrical region of the extension 7, a pin 35 of circular cross section extends through the receiving space 14. The pin 35 is inserted in lateral openings 36 in the wall of the extension 7 and fixed there in a suitable way, for example, by welding or adhesive bonding. The outer diameter of the pin 35 corresponds substantially to the diameter of the recesses 31, 32 having the shape of a segment of a circle.

In order to connect a tip 15 to a leg 2, the tip 15 is inserted, with the proximal ends of the arms 22, 23 first, into the receiving space 14. The slide surfaces 29, 30 thereby engage the pin 35 extending transversely through the receiving space 14 and turn the tip 15 in such a way that both slide surfaces 29, 30 bear with surface-to-surface contact on the pin 35, i.e., the slot 21 is orientated in a precisely defined position so that the longitudinal axis of the pin 35 extends in the center plane of the slot 21. Owing to the pin 35 bearing on the slide surfaces 29, 30, the arms 22, 23, upon further forward movement, are elastically bent apart until the pin 35 snaps into the recesses 31, 32 and is received in these. The arms 22, 23 then spring back into the initial position and hold the pin 35 within the two recesses 31, 32. Further insertion of the tip 15 is prevented by the fact that the edge 33 is constructed higher than the edge 34 of the recesses 31, 32. Conversely, it is, however, possible for the tip, which is normally held in the leg 2 so that it is secured in the axial direction and against rotation by the engagement of the pin 35 in the recesses 31 and 32, to also be pulled out of the leg 2 again. This requires a certain extraction force, which is sufficient to allow the pin 35 to exit from the recesses 31, 32, during which the arms 22 and 23 are elastically bent open again. Since the edge 34 is constructed lower than the edge 33, such extraction is possible, but it is necessary to pull hard on the tip.

The tip 15 inserted in the receiving space 14 is held in the receiving space, firstly, by engagement of the pin 35 in the recesses 31, 32 and, secondly, also by the cylindrical region of the holder 17 bearing against the inner wall of the conical region 13 of the extension 7, more specifically, by the extension 7 engaging at its distal end the outer wall of the holder 17 and thereby guiding the holder 17 laterally.

In the illustrated embodiment, the leg 2 and the extension 7 adjoining it are surrounded by an insulating jacket 37 made of insulating plastic material, which extends as far as the distal end of the extension 7 and may have the shape of a heat shrinkable tube.

In a similar way, the holder is also surrounded by an insulating jacket 38. This extends in the proximal direction as far as the circumferential groove 25.

The gap between the distal end of the insulating jacket 37 and the proximal end of the insulating jacket 38 is covered by a ring-shaped sealing collar 39, which carries a bead-shaped, circumferential ring shoulder 40 on its inner side. This ring shoulder 40 engages the circumferential groove 25 and thereby secures the sealing collar 39 against axial displacement. Thus, when pulling the tip 15 out of the leg 2, the sealing jacket 39 can also be withdrawn with it. This means that when a tip is exchanged, the sealing collar is also exchanged with it.

The invention claimed is:

1. Surgical instrument comprising:
   two legs movable relative to each other, a tip inserted in a receiving space at a distal free end of each of the legs being exchangeably held at the distal free end of said legs;
   a two part fixing device for releasable fixation of each of the tips to the corresponding leg, said fixing device having on one of the two parts two locking arms which are arranged next to each other and are elastically bendable apart, and having on the other one of the two parts a locking projection extending into said leg transversely to a direction of insertion of said tip, said locking projection, when inserting said tip into the receiving space of said leg, engaging between said two locking arms, bending these elastically apart, and, at the end of an inserting movement, entering a recess on an inner side of said locking arms, so that said locking arms approach each other again after they have been elastically bent apart;
   wherein:
   an inner wall of the receiving space at an open insertion end of the receiving space bears tightly against an outside of the tip inserted in said receiving space,
   said receiving space widens in a proximal direction from the open insertion end of said receiving space up to an area extending along at least a partial extent of the locking arms to provide an interior spacing permitting the bending apart of free ends of the locking arms when engaging with or disengaging from the locking projection; and
   the receiving space is a closed receiving space once the tip is inserted into the corresponding leg.

2. Surgical instrument in accordance with claim 1, wherein the inner wall of the receiving space widens conically from the open insertion end in the proximal direction.

3. Surgical instrument in accordance with claim 1, wherein the locking arms have on the inner side between the free ends of the locking arms and the recess a slide surface extending obliquely in relation to the direction of insertion, so that a mutual spacing between the two slide surfaces facing each other increases in a direction towards the free end of the locking arms.

4. Surgical instrument in accordance with claim 1, wherein the mutual spacing between continuations of the recess that are closer to the free ends of the locking arms into the inner side of the locking arms is greater than the mutual spacing between continuations of the recess that are remote from the free ends into the inner side of the locking arms.

5. Surgical instrument in accordance with claim 4, wherein a gap between the tip inserted in the receiving space and the distal free end of the leg is covered by a sealing collar.

6. Surgical instrument in accordance with claim 1, wherein the locking projection is a pin extending transversely to the direction of insertion.

7. Surgical instrument in accordance with claim 1, wherein the locking projection has a circular cross section.

8. Surgical instrument in accordance with claim 7, wherein the recess has a cross section of a segment of a circle.

9. Surgical instrument in accordance with claim 8, wherein a radius of the circular locking projection and of the circular segment of the recesses is substantially identical.

10. Surgical instrument in accordance with claim 1, wherein the recess has a cross section of a segment of a circle.

11. Surgical instrument in accordance with claim 1, wherein the locking arms are firmly connected to the tip, and the locking projection is firmly connected to the leg.

12. Surgical instrument in accordance with claim 11, wherein the locking arms are formed integrally with the tip or with a holder of the tip and are separated from each other by a slot extending from the free ends of the locking arms beyond the recess.

13. Surgical instrument in accordance with claim 11, wherein the locking projection extends transversely through the receiving space.

14. Surgical instrument in accordance with claim 1, wherein a gap between the tip inserted in the receiving space and the distal free end of the leg is covered by a sealing collar.

15. Surgical instrument in accordance with claim 14, wherein the sealing collar is secured in the direction of insertion of the tip by a locking connection comprising a fixing recess and a fixing projection engaging in the fixing recess.

* * * * *